United States Patent

Bhatt et al.

[11] Patent Number: 5,286,477
[45] Date of Patent: Feb. 15, 1994

[54] AEROSOL HAIR STYLING AID

[75] Inventors: Devendra C. Bhatt, Schaumburg; Kathleen A. Kochevar, Wheeling, both of Ill.

[73] Assignee: Helene Curtis, Inc., Chicago, Ill.

[21] Appl. No.: 924,086

[22] Filed: Aug. 3, 1992

Related U.S. Application Data

[63] Continuation-in-part of Ser. No. 716,710, Jun. 18, 1991, abandoned.

[51] Int. Cl.$^5$ ................................................. A61K 7/11
[52] U.S. Cl. ............................................ 424/47; 424/71; 424/78.24; 424/DIG. 1; 424/DIG. 2
[58] Field of Search ............... 424/47, 71, 78, DIG. 1, 424/DIG. 2

[56] References Cited

U.S. PATENT DOCUMENTS

| | | | |
|---|---|---|---|
| 3,405,084 | 10/1963 | Bohac et al. | 260/29.6 |
| 4,261,972 | 4/1981 | Nandagiri et al. | 424/47 |
| 4,767,613 | 8/1988 | Nuber et al. | 424/47 |
| 4,834,968 | 5/1989 | Bolich, Jr. | 424/47 |
| 5,021,238 | 6/1991 | Martino et al. | 424/47 |
| 5,053,218 | 10/1991 | Shernov | 424/47 |
| 5,160,729 | 11/1992 | Login et al. | 424/47 |
| 5,164,177 | 11/1992 | Bhatt et al. | 424/47 |
| 5,176,898 | 1/1993 | Goldberg et al. | 424/47 |
| 5,196,188 | 3/1993 | Potthoff-Karl | 424/47 |
| 5,223,247 | 6/1993 | Kopolow et al. | 424/47 |

FOREIGN PATENT DOCUMENTS

0205306A3 12/1986 European Pat. Off. .
0418676A1 3/1991 European Pat. Off. .

*Primary Examiner*—Paul R. Michl
*Assistant Examiner*—Amy Hulina
*Attorney, Agent, or Firm*—Marshall, O'Toole, Gerstein, Murray & Borun

[57] ABSTRACT

An aqueous aerosol hair spray styling aid composition and method including a terpolymer of vinylpyrrolidone/ethyl methacrylate/methacrylic acid (at least partially neutralized 30-100% monomers in an amount of about 1% to about 12% by weight of the composition, particularly about 2% to about 10% by weight of the composition; water in an amount of about 20% to about 80% by weight of the composition; and a dimethyl ether liquefied propellant gas in an amount of about 25% to about 40% based on the total weight of the aerosol composition.

17 Claims, No Drawings

AEROSOL HAIR STYLING AID

CROSS REFERENCE TO RELATED APPLICATION

This application is a continuation-in-part of co-pending application Ser. No. 07/716,710 filed Jun. 18, 1991, now abandoned.

FIELD OF THE INVENTION

The present invention is directed to an aerosol hair spray styling aid that is sprayed onto the hair from an aerosol composition, containing a dimethyl ether propellant, to provide the hair with a particular shape or configuration. More particularly, the present invention is directed to an aerosol hair spray styling aid including dimethyl ether as the propellant in an amount of at least about 25% by weight of the composition. The aerosol hair spray composition includes a terpolymer of vinylpyrrolidone, ethyl methacrylate and methacrylic acid (at least partially neutralized) monomers and has a very low percentage of volatile organic compounds and a high percentage of water capable of homogeneously dispersing a relatively high percentage of the terpolymer, with or without a water evaporation agent, such as an alcohol, for example, ethanol.

BACKGROUND OF THE INVENTION ART

Hair sprays provide human hair with a particular shape or configuration and function by applying a thin film of a resin or gum onto the hair to adhere adjacent hairs together so that they retain the particular shape or configuration at the time of application. Many of these hair sprays have been applied from aerosol compositions that include a liquefiable propellant gas - generally a halohydrocarbon, such as trichlorofluoromethane or trichlorotrifluoroethane or a gaseous hydrocarbon such as propane or butane. Recently proposed legislation, directed to the depletion of the atmospheric ozone layer has led to the halohydrocarbons being increasingly replaced with pure gaseous non-halogenated hydrocarbons as propellants. However, the use of non-halogenated hydrocarbons as propellants has resulted in a problem of decreased solubility of the hair spray resin or gum in water requiring an increased amount of volatile organic solvent, such as ethanol, to achieve sufficient solubility, therefore creating an additional ecological problem.

As set forth in the Nuber, et al. U.S. Pat. No. 4,767,613, a film-forming terpolymer of vinylpyrrolidone, t-butyl methacrylate and methacrylic acid monomers can be at least partially neutralized to improve the water solubility or dispersibility of the resin and provide the resin with the quality of being easier to remove from the hair during washing. However, as disclosed in the Nuber, et al. U.S. Pat. No. 4,767,613, such aerosol hair treating agents generally have a maximum of about 5% water and require a high amount, up to about 95% by weight, of a volatile organic solvent, such as alcohol, despite the increased solubility of the neutralized resin.

As stated in the product literature of Stepan Company, of Northfield, Ill., directed to the use of the terpolymer of vinylpyrrolidone/ethyl methacrylate/methacrylic acid (STEPANHOLD EXTRA) for use as a fixative hair spray, this particular fixative polymer was designed specifically for pump sprays, not aerosol hair sprays. The terpolymer apparently was not found to be compatible with hydrocarbon propellants, or required far too much alcohol solvent to satisfy volatile organic contaminant regulations. Surprisingly, in accordance with the present invention, it has been found that excellent and homogeneous delivery of the terpolymer can be achieved with the use of dimethyl ether as the propellant.

Stepan Company discloses one example of an aerosol hair spray that includes the terpolymer of the composition of the present invention and has 41.10% by weight water, but the composition also includes 45.70% by weight alcohol, as follows, where percentages are percent by weight: Terpolymer of polyvinylpyrrolidone, ethyl methacylate, and methacrylic acid 9.60%; SDA 40 Alcohol (190 Proof) 45.70%; AMP (Regular) 0.40%; Silicone L-722 (Union Carbide) 0.50%; Propylene Glycol 2.00%; Perfume V-5177 (Van Dyke) 0.60%; 54 Morpholine in SDA 40 Alcohol 0.10%; and Distilled Water 41.10%.

In accordance with the present invention, a new and improved aerosol hair spray styling aid composition has been found wherein a terpolymer of vinylpyrrolidone/ethyl methacrylate/methacrylic acid —at least partially neutralized for water solubility; and about 25% to about 50% dimethyl ether propellant, particularly at least about 25%, to about 40% by weight dimethyl ether propellant and preferably about 25% to about 35% by weight dimethyl ether propellant; can be suitably solubilized or dispersed in the aerosol composition containing about 30% to about 80% water and less than 40% volatile organic compounds (such as alcohol solvents and/or propellants), particularly less than about 35% volatile organic compounds (excluding the propellant), e.g., 0–30% ethanol, preferably 5–25% alcohol, while providing an aerosol spray styling aid that can effectively solubilize or disperse from about 1% to about 12%, by weight of the composition, of the terpolymer, more suitably about 2% to about 10% by weight terpolymer, and preferably about 2% to about 8% by weight terpolymer, with a volatile organic compound, e.g., alcohol, being optionally included for fast drying.

SUMMARY OF THE INVENTION

In brief, the present invention is directed to an aqueous aerosol hair spray styling aid composition and method including a terpolymer of vinylpyrrolidone/ethyl methacrylate/methacrylic acid (at least partially neutralized 30–100%) monomers in an amount of about 1% to about 12% by weight of the composition, particularly about 2% to about 10% by weight of the composition, and especially about 4% to about 8% terpolymer; water in an amount of about 20% to about 80% by weight of the composition; and a dimethyl ether liquefied propellant gas in an amount of about 25% to about 50% based on the total weight of the aerosol composition, preferably about 25% to about 35% by weight dimethyl ether propellant. To achieve the full advantage of the present invention, the methacrylic acid monomer of the terpolymer should be neutralized about 30% to about 100% by weight.

Accordingly, one aspect of the present invention is to provide a new and improved aerosol hair spray composition, and method, that can be applied to the hair from an aqueous aerosol composition in the form of a hair spray, that provides hair setting compositions for retaining a particular shape or configuration of the hair.

Another aspect of the present invention is to provide an aerosol hair spray styling aid composition, and method, in the form of a hair spray, that includes water in an amount of about 30% to about 90% by weight of the composition, a fixative resin that is solubilized or dispersed in an amount of about 1% to about 12% by weight of the composition, and a dimethyl ether propellant gas, in an amount of at least about 25% by weight to about 35% by weight.

Another aspect of the present invention is to provide an aerosol hair spray styling aid composition, and method, in the form of a hair spray, that includes at least 30% by weight water, a fixative resin comprising a terpolymer of vinylpyrrolidone/ethyl methacrylate/methacrylic acid and a dimethyl ether propellant.

Still another aspect of the present invention is to provide a new and improved aerosol hair spray styling aid composition, and method, that includes water in an amount of about 30% to about 90% by weight of the composition; a fixative resin that is solubilized or dispersed in an amount of about 1% to about 12% by weight of the composition; alcohol in an amount of 0–30%, preferably 5–25%, by weight; dimethyl ether propellant gas in an amount of about 25% to about 35% by weight; and a conditioning agent in an amount of about 0.1% to about 10% by weight of the composition.

DETAILED DESCRIPTION OF THE PREFERRED EMBODIMENTS

The aerosol hair spray styling aid composition of the present invention include about 1% to about 12% by weight of a terpolymer of vinylpyrrolidone/ethyl methacrylate/methacrylic acid —at least partially neutralized for water solubility; and at least about 25% to about 35% by weight dimethyl ether propellant; about 30% to about 80% water and less than 40% volatile organic compounds (e.g., alcohol solvent and/or propellant), particularly less than about 35% alcohol, e.g., 0–30% ethanol, preferably 5–25% alcohol. Surprisingly, the composition provides an aerosol hair spray styling aid that can effectively solubilize or disperse up to about 12% by weight of the composition of the terpolymer, preferably about 2% to about 10% by weight terpolymer, to provide a fine spray capable of homogeneous deposition of the terpolymer, with a volatile organic compound, e.g., alcohol, being optionally included for faster drying.

Mixtures of the vinylpyrrolidone/ethyl methacrylate/methacrylic acid terpolymer with other polymers also may be used provided that the terpolymer is present in an amount of at least 50%, preferably at least 75% by weight of total fixative resin in the aerosol composition. With certain of the polymers, it may be necessary to neutralize some acidic groups to promote solubility/dispersibility, e.g., PVA/crotonic acid. Neutralization and increased solubilization are accomplished with one or more inorganic bases such as sodium hydroxide, potassium hydroxide, ammonium hydroxide and/or ammonium carbonate. Among stable organic bases are the water soluble bases such as monoethanol amine (MEA), diethanol amine (DEA), triethanol amine (TEA), 2-methyl-2-amino-1-propanol (AMP), mono Amino glycols, and the like, which help solubilize the polymer in water solutions. The terpolymer of the composition and method of the present invention is sufficiently soluble at about 60% neutralization without the inclusion of an alcohol solvent and at about 30% neutralization when at least about 5% alcohol by weight, e.g., ethanol is included in the composition. The terpolymer can be sufficiently neutralized using about 0.2% to about 5% by weight of a base, based on the total weight of the aerosol composition. The pH of these solutions usually ranges from about 5 to about 12. Neutral pH's of about 6 to about 9 are preferred.

The terpolymer, and optionally other combined fixative resins, is used at a level of from about 1% to about 12%, by weight, usually in an amount of about 2% to about 10% by weight, and preferably about 2% to about 8% of the total weight of the composition. The weight average molecular weight of the terpolymer is not critical but is generally in the range of from about 2,000 to about 2,000,000.

In accordance with one important embodiment of the present invention, the composition of the present invention also includes from about 0.1% to about 10%, particularly about 0.5% to about 10%, and preferably from about 1.0% to about 5.0%, by weight of a non-volatile silicone compound or other conditioning agent(s), preferably a water-insoluble, emulsifiable conditioning agent. The preferred non-volatile silicone compound is a polydimethylsiloxane compound, such as a mixture, in about a 3:1 weight ratio, of a low molecular weight polydimethylsiloxane fluid and a higher molecular weight polydimethylsiloxane gum. The non-volatile polydimethylsiloxane compound is added to the composition of the present invention in an amount sufficient to provide improved combing and improved feel (softness) to the hair after shampooing. As referred to herein, "silicone gums" are those nonfunctional siloxanes having a viscosity of from about 5 to about 600,000 centistokes at 25° C. The so-called rigid silicones, as described in U.S. Pat. No. 4,902,499, herein incorporated by reference, having a viscosity above 600,000 centistokes at 20° C., e.g., 700,000 centistokes plus, and a weight average molecular weight of at least about 500,000 also are useful in accordance with the present invention.

Preferred silicone gums include linear and branched polydimethylsiloxanes, of the following general formula:

$$(CH_3)_3SiO-[Si(CH_3)_2O]_n-Si(CH_3)_3,$$

wherein n is from about 2,000 to about 15,000, preferably from about 2,000 to about 7,000. Silicone gums useful in compositions of the present invention are available from a variety of commercial sources, including General Electric Company and Dow Corning.

Another particularly suitable conditioning agent that can be included in the composition of the present invention is a volatile hydrocarbon, such as a hydrocarbon including from about 10 carbon atoms to about 30 carbon atoms, that has sufficient volatility to slowly volatilize from the hair after application of the aerosol styling aid composition. The volatile hydrocarbons provide essentially the same benefits as the silicone conditioning agents.

The preferred volatile hydrocarbon compound is an aliphatic hydrocarbon including from about 12 to about 24 carbon atoms, and having a boiling point in the range of from about 100° C. to about 300° C. Exemplary volatile hydrocarbons are depicted in general structural formula (I), wherein n ranges from 2 to 5,

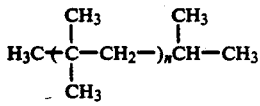

(I)

Examples of volatile hydrocarbons useful in the composition of the present invention are the commercially-available compounds PERMETHYL 99A and PERMETHYL 101A, corresponding to compounds of general structure (I) wherein n is 2 and 3, respectively, available from Permethyl Corporation, Frazer, Pa. A volatile hydrocarbon compound is useful in the composition of the present invention either alone, or in combination with another volatile hydrocarbon, or in combination with a volatile silicone.

Examples of other suitable water-insoluble conditioning agents that can be incorporated into the aqueous aerosol styling aid composition of the present invention include the following: polysiloxane polyether copolymers; polysiloxane polydimethyl dimethylammonium acetate copolymers; acetylated lanolin alcohols; dimethyl dialkyl ammonium chloride; lauryl dimethylamine oxide; stearyl dimethyl benzyl ammonium chloride; lanolin-derived extract of sterols and sterol esters; lanolin alcohol concentrate; isopropyl ester of lanolin fatty acids; sulfur rich amino acid concentrate; isopropyl ester of lanolin fatty acids; stearyl dimethyl benzyl ammonium chloride; cetyl trimethyl ammonium chloride; oleyl dimethyl benzyl ammonium chloride; oleyl alcohol; stearyl alcohol; stearyl dimethyl benzyl ammonium chloride; stearamido propyl dimethyl myristyl acetate ammonium chloride; polyol fatty acid; fatty amido amine; guar hydroxypropyltrimonium chloride; cetyl/-stearyl alcohol; quaternized protein, keratin protein derivatives; isostearamido propyl dimethylamine; stearamido propyl dimethylamine; myristrimonium bromide; cetrimonium bromide; myristrimonium bromide; stearalkonium chloride; cetyl trimethyl ammonium chloride; laurylpyridinium chloride; tris (oligoxyethyl) alkyl ammonium phosphate; amino functional silicones; lapyrium chloride; isopyropyl ester of lanolic acids; ethoxylated (30) caster oil; acetyated lanolin alcohol; fatty alcohol fraction of lanolin; mineral oil and lanolin alcohol mixture; esters of lanolin; quaternium-75; vinylpyrrolidone/dimethylamino-ethyl methacrylate copolymer; alkyl trimethyl ammonium chloride; 5 mole ethylene oxide adduct of soya sterol; 10 mole ethylene oxide adduct of soya sterol; stearic acid ester of ethoxylated (20 mole) methyl glucoside; sodium salt of polyhydroxycarboxylic acid; hydroxylated lanolin; cocamidropropyl dimethylamine lactate; cocamidopropyl dimethylamine propionate; cocamidopropyl morpholine lactate; isostearamidopropyl dimethylamine lactate; isostearamidopropyl morpholine lactate; oleamidopropyl dimethylamine lactate; linoleamidopropyl dimethylamine lactate; stearamidopropyl dimethylamine lactate, ethylene glycol monostearate and propylene glycol mixture; stearamidopropyl dimethylamine lactate; acetamide MEA; lactamide MEA; stearamide MEA; behanalkonium chloride; behenyl trimethyl ammonium methosulfate and cetearyl alcohol mixture; cetearyl alcohol; isostearamidopropalkonium chloride; linoleamidopropalkonium chloride; oleyl dimethyl benzyl ammonium chloride; tallow imidazolinum methosulfate; stearyl dimethyl benzyl ammonium chloride; stearyl trimonium methosulfate; mixed ethoxylated and propoxylated long chain alcohols; stearamidopropyl dimethylamine lactate; polonitomine oxide; oleamine oxide; stearamine oxide; soya ethyldimonium ethosulfate; hydroxypropyl bislauryl-dimonium chloride; hydroxypropyl biscetyl-dimonium chloride; hydroxypropyl bisstearyl dimonium chloride; hydroxypropyl bisbehenyl dimonium chloride; ricinolamido propyl ethyldimonium ethosulfate; olealkonium chloride; stearalkonium chloride; N-(3-Isostearamido propyl)-N,N-dimethyl amino glycolate; N-(3-Isostearamido propyl)-N,N dimethyl amino gluconate; hydrolyzed animal keratin; ethyl hydrolyzed animal keratin; stearyl ammonium chloride; stearamidoethyl diethylamine; cocamidopropyl dimethylamine; lauramidopropyl dimethylamine; oleamidopropyl dimethylamine; palmitamidopropyl dimethylamine; stearamidopropyl dimethylamine lactate; avocado oil; almond oil, grape seed oil; jojoba oil; apricot kernel oil; sesame oil; hybrid safflower oil; wheat germ oil; cocamidoamine lactate; ricinoleamido amine lactate; stearamido amine lactate; stearamido morpholine lactate; isostearamido amine lactate; isostearamido mopholine lactate; wheat germamido-dimethylamine lactate; behenamido-propyl betaine; ricinoleamidopropyl betaine; wheat germamido propyl dimethylamine oxide; disodium isostearamido MEA sulfosuccinate; disodium oleamide PEG-2 sulfosuccinate; disodium oleamide MEA sulfosuccinate; disodium ricinolyl MEA sulfosuccinate; disodium wheat germamido, MEA sulfosuccinate; disodium wheat germamido PEG-2 sulfosuccinate; stearalkonium chloride; stearyl dimethyl benzyl ammonium chloride; stearamido amine; stearamido morpholine; isostearamido amine; isostearamido morpholine; polyethyleneglycol (400) mono and distearates; synthetic calcium silicate; isostearic alkanolamide; ethyl esters of hydrolyzed animal protein; blend of cetyl, stearyl alcohols with ethoxylated cetyl or stearyl alcohols; amido amines; polyamido amines; palmityl amido betaine; propoxylated (1-20 moles) lanolin alcohols; isostearamide DEA; and hydrolyzed collagen protein.

When one or more of these water-insoluble conditioning agents is included in the composition of the present invention in an amount of about 0.5% to about 10% by total weight of the composition, the composition also can include a suspending agent for the conditioning agent, in an amount of about 0.5% to about 10%, by total weight of the composition. The particular suspending agent is not critical and can be selected from any materials known to suspend water-insoluble liquids in shampoo compositions. Suitable suspending agents are, for example, dehydrogenated tallow phthalic acid amide (distearyl phthalamic acid); fatty acid alkanolamides; esters of polyols and sugars; polyethylene glycols; the ethoxylated or propoxylated alkylphenols; ethoxylated or propoxylated fatty alcohols; and the condensation products of ethylene oxide with long chain amides. These suspending agents, as well as numerous others not cited herein, are well known in the art and are fully described in the literature, such as McCUTCHEON'S DETERGENTS AND EMULSIFIERS, 1989 Annual, published by McCutcheon Division, MC Publishing Co.

A nonionic alkanolamide also is optionally included in an amount of about 0.1% to about 5% by weight in the aerosol styling aid compositions that include a conditioning agent to provide exceptionally stable emulsification of water-insoluble conditioning agents and to aid in thickening and foam stability. Other useful suspending and thickening agents can be used instead of the alkanolamides such as sodium alginate; guar gum; xanthan gum; gum arabic, cellulose derivatives, such as methylcellulose, hydroxybutylcellulose, hydroxyethylcellulose, hydroxypropylcellulose and carboxymethylcellulose; and various synthetic polymeric thickeners, such as the polyacrylic acid derivatives. Suitable alkanolamides include, but are not limited to, those known in the art of hair care formulations, such as cocamide monoethanolamide (MEA), cocamide diethanolamide (DEA), soyamide DEA, lauramide DEA, oleamide monoisopropylamide (MIPA), stearamide MEA, myristamide MEA, lauramide MEA, capramide DEA, ricinoleamide DEA, myristamide DEA, stearamide DEA, oleylamide DEA, tallowamide DEA, lauramide MIPA, tallowamide MEA, isostearamide DEA, isostearamide MEA and combinations thereof. Other suitable suspending agents are disclosed in Oh, et al. U.S. Pat. No. 4,704,272; Grote, et al. U.S. Pat. No. 4,741,855; and Bolich, Jr., et al. U.S. Pat. No. 4,788,006, which patents are hereby incorporated by reference.

Emulsion stabilizers also may be used in compositions of the invention. Useful examples include, such compounds as polyethylene glycol, silicone copolyols, polyvinyl alcohol, sorbitan monostearate, oleth-2, sorbitan monolaurate, and nonionic block copolymers of ethylene oxide and propylene oxide such as those marketed by BASF Wyandotte under the name PLURONICS ®. When present, such stabilizers comprise from about 0.05% to about 1%, preferably from about 0.1% to about 0.8%.

The amount of the dimethyl ether propellant gas used in the hair spray composition and method of the present invention is from at least about 25% by weight to about 35% by weight, preferably from about 25% to about 30% by weight of the total composition. If the dimethyl ether propellant includes a vapor pressure suppressant (e.g., trichloroethane or dichloromethane), for weight percentage calculations, the amount of suppressant is included as part of the propellant.

The aerosol hair spray compositions also can contain a variety of other nonessential, optional components suitable for rendering such compositions more acceptable. Such conventional optional ingredients are well known to those skilled in the art, e.g., other emulsifiers such as anionics (e.g., sodium alkyl sulfate); preservatives such as benzyl alcohol, methyl paraben, propyl paraben and imidazolidinylurea; cationic emulsifiers/conditioners such as cetyl trimethyl ammonium chloride, stearyldimethyl benzyl ammonium chloride, and di(partially) hydrogenated tallow, dimethylammonium chloride; thickeners and viscosity modifiers such as a diethanolamide of a long chain fatty acid, fatty alcohols (i.e., cetearyl alcohol), sodium chloride, sodium sulfate, and ethyl alcohol; pH adjusting agents such as citric acid, succinic acid, sodium hydroxide and triethanolamine; coloring agents such as any of the FD&C or D&C dyes; hair oxidizing (bleaching) agents such as hydrogen peroxide, perborate salts and persulfate salts; hair reducing agents such as thioglycolates; perfume oils; chelating agents such as ethylenediamine tetracetic acid; and, among many other agents, polymer plasticizing agents such as glycerin and propylene glycol. These optional materials are generally used individually at a level of from about 0.01% to about 19%, preferably from about 0.5% to about 5% by weight of the total composition.

The aqueous formulations of the present invention also can contain the conventional hair spray adjuvants in amounts which generally range from about 0.1% to about 2% by weight and preferably about 0.75% to 1% by weight. Among the additives which can be used are plasticizers such as glycols, phthalate esters and glycerine; silicones; emollients; lubricants and penetrants such as various lanolin compounds; protein hydrolysates and other protein derivatives; ethylene adducts and polyoxyethylene cholesterol; dyes, tints and other colorants; and perfumes.

The optional alcohol employed in the composition is an aliphatic straight or branched chain monohydric alcohol having 2 to about 4 carbon atoms. Isopropanol and especially ethanol are preferred. The concentration of the alcohol in the composition should be less than about 40% by weight, and surprisingly can be as low as 0%, preferably about 0.1% to about 30% by weight and more preferably about 5% to about 20% by weight. Some alcohol, in an amount of about 2% to about 25% by weight provides faster drying of the hair spray styling aid after application to the hair.

Suitable compositions in accordance with the present invention are as follows:

| COMPONENT | WT. % |
| --- | --- |
| 1. terpolymer of vinylpyrrolidone/ethyl methacrylate/methacrylic acid fixative resin | 4.20 |
| 2. neutralizing agent, e.g., 2-methyl-2-amino-1-propanol (AMP) | 0.30 |
| 3. ethyl alcohol solvent | 30.20 |
| 4. dimethyl ether propellant | 30.00 |
| 5. distilled water | 35.00 |
| 6. dimethicone silicone conditioning agent | 0.20 |
| 7. fragrance | 0.10 |
| | 100.00 |
| 1. terpolymer of vinylpyrrolidone/ethyl methacrylate/methacrylic acid fixative resin | 4.80 |
| 2. neutralizing agent, e.g., 2-methyl-2-amino-1-propanol (AMP) | 1.00 |
| 3. ethyl alcohol solvent | 12.20 |
| 4. dimethyl ether propellant | 25.00 |
| 5. distilled water | 56.73 |
| 6. dimethicone silicone conditioning agent | 0.15 |
| 7. fragrance | 0.12 |
| | 100.00 |

Other suitable compositions that can be formed in accordance with the present invention, that include little or no alcohol are as follows:

| COMPONENT | WT. % |
| --- | --- |
| 1. terpolymer of vinylpyrrolidone/ethyl methacrylate/methacrylic acid fixative resin | 12.00 |
| 2. neutralizing agent, e.g., 2-methyl-2-amino-1-propanol (AMP) | 1.00 |
| 3. ethyl alcohol solvent | 5.00 |
| 4. dimethyl ether propellant | 25.00 |
| 5. distilled water | 56.73 |
| 6. dimethicone silicone conditioning agent | 0.15 |
| 7. fragrance | 0.12 |
| | 100.00 |
| 1. terpolymer of vinylpyrrolidone/ethyl methacrylate/methacrylic | 8.00 |

| COMPONENT | WT. % |
| --- | --- |
| acid fixative resin | |
| 2. neutralizing agent, e.g., 2-methyl-2-amino-1-propanol (AMP) | 2.00 |
| 3. ethyl alcohol solvent | 2.00 |
| 4. dimethyl ether propellant | 35.00 |
| 5. distilled water | 51.80 |
| 6. blend of silicone conditioning agents: 25% SE-30 Gum 75% SF-96-50 Oil | 1.00 |
| 7. fragrance | 0.20 |
| | 100.00 |

What is claimed is:

1. An aerosol hair spray composition comprising a fixative resin comprising a terpolymer of vinylpyrrolidone/ethyl methacrylate/methacrylic acid, neutralized at least 30%, in an amount of about 1% to about 12% by weight of the composition; water in an amount of about 30% to about 90% by weight of the composition; dimethyl ether propellant in an amount of about 25% to about 35% by weight of the composition; and 0–30% alcohol.

2. The composition of claim 1 further including a conditioning agent in an amount of about 0.1% to about 10% by weight of the composition.

3. The composition of claim 2, wherein the conditioning agent is water-insoluble and selected from the group consisting of a silicone conditioning agent, a volatile hydrocarbon conditioning agent, and mixtures.

4. The composition of claim 3 further including a water-insoluble alkanolamide in an amount of about 0.1% to about 5% by weight of the composition.

5. The composition of claim 1 further including an emulsion stabilizer in an amount of about 0.05% to about 3% by weight of the composition selected from the group consisting of a glycol, glycerine, a silicone copolyol, polyvinyl alcohol, sorbitan monostearate, oleth-2, sorbitan monolaurate, a copolymer of ethylene oxide and propylene oxide, and mixtures.

6. The composition of claim 1, wherein the alcohol is a straight or branched chain monohydric alcohol having 2 to about 4 carbon atoms and is included in the composition in an amount of about 1% to about 30% by weight of the composition.

7. The composition of claim 6, wherein the alcohol is included in an amount of about 5% to about 25% by weight of the composition.

8. An aerosol hair spray composition comprising a fixative resin comprising a terpolymer of vinylpyrrolidone, ethyl methacrylate, and methacrylic acid in an amount of about 1% to about 12% by weight of the composition; water in an amount of about 30% to about 90% by weight of the composition; dimethyl ether propellant in an amount of about 25% to about 35% by weight of the composition; 0–30% alcohol; and about 0.1% to about 5% neutralizing agent for the terpolymer sufficient to neutralize at least 30% of the acidic groups in the terpolymer.

9. A method of fixing human hair in a desired configuration comprising applying an aerosol spray composition containing a fixative resin to the hair, while said hair is in said desired configuration, to adhere adjacent hairs together, said fixative resin comprising a terpolymer of vinylpyrrolidone/ethyl methacrylate/methacrylic acid in an amount of about 1% to about 12% by weight of the composition, said terpolymer neutralized at least 30%, water in an amount of about 30% to about 90% by weight of the composition; dimethyl ether propellant in an amount of about 25% to about 35% by weight of the composition; and 0–30% alcohol.

10. The method of claim 9, wherein the composition further includes a conditioning agent in an amount of about 0.1% to about 10% by weight of the composition.

11. The method of claim 10, wherein the conditioning agent is water-insoluble and selected from the group consisting of a silicone conditioning agent, a volatile hydrocarbon conditioning agent, and mixtures.

12. The method of claim 11, wherein the composition further includes a water-insoluble alkanolamide in an amount of about 0.1% to about 5% by weight of the composition.

13. The method of claim 9, wherein the composition further includes an emulsion stabilizer in an amount of about 0.05% to about 3% by weight of the composition selected from the group consisting of a glycol, glycerine, a silicone copolyol, polyvinyl alcohol, sorbitan monostearate, oleth-2, sorbitan monolaurate, a copolymer of ethylene oxide and propylene oxide, and mixtures.

14. The method of claim 9, wherein the alcohol is a straight or branched chain monohydric alcohol having 2 to about 4 carbon atoms and is included in the composition in an amount of about 1% to about 30% by weight of the composition.

15. The method of claim 9, wherein the alcohol is included in an amount of about 5% to about 25% by weight of the composition.

16. An aqueous aerosol hair spray composition containing no alcohol comprising a fixative resin comprising a terpolymer of vinylpyrrolidone, ethyl methacrylate, and methacrylic acid, neutralized at least 30% in an amount of about 1% to about 12% by weight of the composition; water in an amount of about 30% to about 90% by weight of the composition; and dimethyl ether propellant in an amount of about 25% to about 35% by weight of the composition.

17. A hydroalcoholic aerosol hair spray composition comprising a fixative resin comprising a terpolymer of vinylpyrrolidone, ethyl methacrylate, and methacrylic acid, neutralized at least 30%, in an amount of about 1% to about 12% by weight of the composition; water in an amount of about 30% to about 90% by weight of the composition; dimethyl ether propellant in an amount of about 25% to about 35% by weight of the composition; and about 0.5% to about 20% by weight alcohol.

* * * * *